United States Patent [19]

Möller et al.

[11] 4,439,418

[45] Mar. 27, 1984

[54] TOPICAL PREPARATIONS FOR THE TREATMENT OF SEBORRHEA AND PROCESS FOR INHIBITING SEBUM PRODUCTION

[75] Inventors: Hinrich Möller; Siegfried Wallat, both of Monheim; Friedhelm Bartnik, Düsseldorf, all of Fed. Rep. of Germany

[73] Assignee: Henkel KGaA, Duesseldorf, Fed. Rep. of Germany

[21] Appl. No.: 329,079

[22] Filed: Dec. 9, 1981

[30] Foreign Application Priority Data

Jul. 29, 1981 [DE] Fed. Rep. of Germany ....... 3129867

[51] Int. Cl.³ .......................... A61K 7/06; A61K 7/15
[52] U.S. Cl. .......................................... 424/70; 424/4; 424/73; 424/358; 424/365; 568/328; 568/331; 568/335; 568/337
[58] Field of Search ............... 568/328, 331, 335, 337; 424/70, DIG. 4

[56] References Cited

U.S. PATENT DOCUMENTS

| | | | |
|---|---|---|---|
| 3,686,319 | 8/1972 | Lafon | 424/331 |
| 3,817,752 | 6/1974 | Laridon et al. | 568/328 |
| 3,879,449 | 4/1975 | Anderson et al. | 424/331 |
| 3,880,932 | 4/1975 | Anderson et al. | 424/331 |
| 3,972,996 | 8/1976 | Pitts et al. | 424/48 |
| 4,326,055 | 4/1982 | Loeliger | 568/328 |

*Primary Examiner*—Dale R. Ore
*Attorney, Agent, or Firm*—Ernest G. Szoke; Nelson Littell, Jr.

[57] ABSTRACT

A topical cosmetic preparation for the treatment of seborrhea containing an antiseborrheically effective amount of at least one compound having the formula

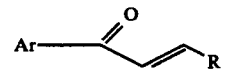

wherein Ar represents a member selected from the group consisting of phenyl, phenyl substituted with at least one group selected from the group consisting of alkyl having from 1 to 4 carbon atoms, alkoxy having from 1 to 4 carbon atoms, hydroxy and halo, naphthyl and heteroaromatic radical having from 4 to 5 carbon atoms in the cycle, and R represents a member selected from the group consisting of hydrogen, alkyl having from 1 to 4 carbon atoms, alkanoyl having from 1 to 4 carbon atoms, aryl and arylcarbonyl, where aryl has the same meaning as Ar, as an antiseborrheic, and further containing conventional vehicles and additives. The invention also relates to the process for reducing sebaceous cell sebum production employing said topical cosmetic preparation.

4 Claims, No Drawings

TOPICAL PREPARATIONS FOR THE TREATMENT OF SEBORRHEA AND PROCESS FOR INHIBITING SEBUM PRODUCTION

BACKGROUND OF THE INVENTION

The subject of the invention is topical cosmetic preparations to improve the greasy and unesthetic appearance of hair and skin, particularly for the treatment of greasy hair.

The excessive secretion of the sebaceous glands of the scalp imparts to the hair a greasy appearance, which is generally considered unesthetic. It has, therefore, been tried to normalize the secretion of the sebaceous glands by suitable preparations to give the hair its healthy appearance. For the treatment of seborrhea, oral preparations have been suggested which contain cysteamine derivatives (DOS 16 67 902). Shampoos with sulfur, mercury or tar have been used against seborrhea affecting the hair on the head. It was found, however, that these preparations frequently have side effects in prolonged use, without really satisfactory results as far as effectiveness or application properties are concerned. German Published Application DOS 19 06 665 suggested N,N-diethyl-m-toluamide as an active substance for the treatment of dandruff caused by seborrhea. U.S. Pat. No. 3,755,604 suggests phenylpentadienoic acids to control the production of sebum. But it was found that neither N,N-diethyl-m-toluamide nor phenylpentadienoic acid show, however, fully satisfactory sebo-suppressive properties.

OBJECTS OF THE INVENTION

An object of the present invention is the development of a topical cosmetic preparation for the treatment of seborrhea and the control of the production of sebum.

Another object of the present invention is the development of a topical cosmetic preparation for the treatment of seborrhea containing an antiseborrheically effective amount of at least one compound having the formula

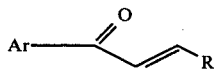

wherein Ar represents a member selected from the group consisting of phenyl, phenyl substituted with at least one group selected from the group consisting of alkyl having from 1 to 4 carbon atoms, alkoxy having from 1 to 4 carbon atoms, hydroxy and halo, naphthyl and heteroaromatic radical having from 4 to 5 carbon atoms in the cycle, and R represents a member selected from the group consisting of hydrogen, alkyl having from 1 to 4 carbon atoms, alkanoyl having from 1 to 4 carbon atoms, aryl and arylcarbonyl, where aryl has the same meaning as Ar, as an antiseborrheic, and further containing conventional vehicles and additives.

A further object of the present invention is the development of a process for reducing sebaceous cell sebum production in a mammal in need thereof which comprises contacting said sebaceous cell in the skin of said mammal with an effective amount to reduce sebum production of at least one compound having the formula

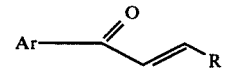

wherein Ar represents a member selected from the group consisting of phenyl, phenyl substituted with at least one group selected from the group consisting of alkyl having from 1 to 4 carbon atoms, alkoxy having from 1 to 4 carbon atoms, hydroxy and halo, naphthyl and heteroaromatic radical having from 4 to 5 carbon atoms in the cycle, and R represents a member selected from the group consisting of hydrogen, alkyl having from 1 to 4 carbon atoms, alkanoyl having from 1 to 4 carbon atoms, aryl and arylcarbonyl, where aryl has the same meaning as Ar.

These and other objects of the invention will become more apparent as the description thereof proceeds.

DESCRIPTION OF THE INVENTION

It has been found that topical cosmetic preparations with a content of compounds of the general formula I

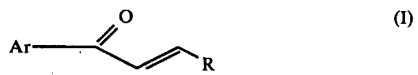

where Ar stands for phenyl, which can be substituted by lower alkyl or lower alkoxy groups with 1 to 4 carbon atoms, hydroxy groups or halogens; a naphthyl radical; or a heteroaromatic radical; like thienyl or furyl, and R stands for hydrogen, an alkyl or alkanoyl with 1 to 4 carbon atoms, aryl or arylcarbonyl, where aryl has the same meaning as Ar, are highly effective in the treatment of seborrheic skin and greasy hair.

More particularly, the present invention relates to a topical cosmetic preparation for the treatment of seborrhea containing an antiseborrheically effective amount of at least one compound having the formula

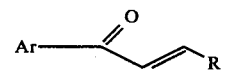

wherein Ar represents a member selected from the group consisting of phenyl, phenyl substituted with at least one group selected from the group consisting of alkyl having from 1 to 4 carbon atoms, alkoxy having from 1 to 4 carbon atoms, hydroxy and halo, naphthyl and heteroaromatic radical having from 4 to 5 carbon atoms in the cycle, and R represents a member selected from the group consisting of hydrogen, alkyl having from 1 to 4 carbon atoms, alkanoyl having from 1 to 4 carbon atoms, aryl and arylcarbonyl, where aryl has the same meaning as Ar, as an antiseborrheic, and further containing conventional vehicles and additives. The invention also relates to the process for reducing sebaceous cell sebum production employing said topical cosmetic preparation.

The aryl ketones utilized in the process of the invention are known from the literature and are partly commercially available. For the preparation of the unsaturated aryl ketones, the carbonylalkenyl radical can be introduced into the aromatic substances by Friedel-Crafts synthesis with a corresponding acid halide. Another possibility for the production of the compounds according to the invention is the aldol-condensation of aldehydes to the corresponding acetyl-aromatic substances. The double bond can also be introduced by dehydrohalogenation or dehalogenation of the corresponding saturated halogen compounds.

Suitable unsaturated aryl ketones used in the process of the invention are, for example, ω-benzalacetophenone, 1-phenyl-prop-2-en-1-one, 1-phenyl-but-2-en-1-one, 1-phenyl-pent-2-en-1-one, 1-phenyl-4,4-dimethyl-pent-2-en-1-one, ω-(p-chlorobenzal)-acetophenone, ω-(p-fluorobenzal)-acetophenone, ω-(p-methoxybenzal)-acetophenone, ω-(p-methylbenzal)-acetophenone, ω-(p-chlorobenzal)-p-chloro-acetophenone, ω-(p-chlorobenzal)-2,4-dichloro-acetophenone, ω-benzal-p-chloro-acetophenone, ω-benzal-p-fluoro-acetophenone, ω-benzal-p-methoxyacetophenone, ω-benzal-p-hydroxy-acetophenone, ω-benzal-2,4-dimethyl-acetophenone, cis-1,2-dibenzoyl-ethene, trans-1,2-dibenzoyl-ethene, trans-1,2-di-(p-chlorobenzoyl)-ethene, trans-1,2-di-(p-tert.butyl-benzoyl)-ethene, trans-1,2-di-(p-methoxy-benzoyl)-ethene, trans-1,2-di-(2,4-dimethyl-benzoyl)-ethene, trans-1,2-di-(2,5-dimethyl-benzoyl)-ethene, trans-1,2-di-(3,4-dimethyl-benzoyl)-ethene, trans-1,2-di(2,4-dihydroxy-benzoyl)-ethene.

The cosmetic preparations according to the invention represent solutions of the effective compounds of formula I in water, in alcohol especially ethanol, in aqueous-alcoholic mixtures, in oil, as well as in suspensions, gels, emulsions, salves, pastes, or aerosols. They can be incorporated in practically any known cosmetic preparation used for the treatment of the skin and hair. Thus, the cosmetic preparations according to the invention can be used in the form of hair tonics, shampoos, hair treatments, hair rinses or in the form of skin lotions and shaking mixtures. In addition to the compounds of formula I, the preparations according to the invention also contain known vehicles and additives, like water, organic solvents, surface-active compounds, oils and fats, waxes, perfume oils, dyes, preservatives, etc. An advantageous form for the treatment of greasy hair is the shampoo. These shampoos can contain, in addition to a compound of the general formula I, anionic, cationic, nonionic, or amphoteric tensides, dyes, perfumes, thickeners, conditioners, etc.

The cosmetic preparations according to the invention contain the unsaturated aryl ketones of formula I in an amount of from 0.01% to 20% by weight, preferably from 0.1% to 1.0% by weight, related to the weight of the total preparation. The preparations according to the invention can be used daily, but satisfactory results are already obtained with a single weekly application. The individual dose to be used in each treatment is not critical. Harmful side effects are not observed. The greasy appearance of the hair is reduced, and fat production delayed, so that normal hair care is possible.

If the preparation according to the invention is used in the form of hair creams or hair milk preparations or shaking mixtures, it is possible to improve the appearance permanently by regular application on the skin.

The following examples will illustrate the subject of the invention without limiting it, however, to these examples.

EXAMPLE

First, production of some of the unsaturated aryl ketones to be used in the preparations according to the invention is described.

PREPARATION A

Trans-1,2-bis-(p-chlorobenzoyl)-ethene

To a stirred suspension of 31 gm (0.23 mol) of aluminum trichloride in 230 ml chlorobenzene, 18 gm (0.12 mol) of fumaryl chloride were added slowly in drops at room temperature. The mixture was stirred for 1.3 hours at room temperature and for another 1.3 hours at 45° C. After introduction into ice-water and acidification with concentrated HCl, the mixture was extracted with 1.5 liters of methylene chloride. After evaporation of the methylene chloride, the residue was washed with about 200 ml of ethanol and recrystallized from acetone. 27 gm (75% of the theory) of trans-1,2-bis-(p-chlorobenzoyl)-ethene were obtained with a melting point of 174°–176° C.

The following compounds were obtained in a similar manner as in Preparation A:

(B) Trans-1,2-dibenzoyl-ethene, m.p. 111° C.

(C) Trans-1,2-bis-(2,4-dimethyl-benzoyl)-ethene, m.p. 128°–130° C.

(D) Trans-1,2-bis-(2,5-dimethyl-benzoyl)-ethene, m.p. 106°–108° C.

(E) Trans-1,2-bis-(3,4-dimethyl-benzoyl)-ethene, m.p. 142°–143° C.

(F) Trans-1,2-bis-(p-methoxy-benzoyl)-ethene, m.p. 162°–164° C.

(G) ω-benzal-acetophenone, m.p. 56°–57° C.

The antiseborrheic action of the compounds used in the preparations according to the invention was further investigated in the following animal tests. Male Wistar rats of 220–230 gm body weight were used as test animals. The degree of browning was judged visually on the backs of the shaved rats. The browning is caused by the surface skin lipid of the rats. This test is based on the observation that young female rats, as well as male rats after washing with a tenside solution or a lipid in solvent, and also male rats which had been treated systematically with estrogens, show only the normal light pink-colored skin after hair-shaving. Parallel thereto, only very small amounts of lipids can be extracted from the hair cut off.

In order to evaluate the sebosuppressive action, the test substances in the form of a 1% solution in ethanol or ethanol/acetone (1:1) were brushed on one side of the back hair of 6 rats. The other side was treated with the solvent without the active substance (control side). During the 14 days of testing the solution was applied one time a day for a total of 9 days. A group of 6 rats which received no treatment at all served as a further control. At the end of the test, the animals were shaved completely on the back and on the sides. Both sets of rats were inspected independently by a jury panel (6 persons) under double blind conditions.

The first criterion evaluated was whether the majority of the judges had correctly recognized the treated side; the following differentiations were made:

| Symbol | % of judges who had recognized an effect |
|--------|------------------------------------------|
| ++     | 100%                                     |
| +      | >50% to 100%                             |
| 0      | ≦50%                                     |

The second criterion was the difference between the right and left side, where 1 point was given per judge and animal, namely so that the darker side was graded with 1 and the lighter side with 0, and if both sides were equal, they were graded with 0.5.

The third criterion was the intensity differences of the brown tones according to the following scale:

3 points—dark brown
2 points—medium brown
1 point—weak brown
0 points—no brown coloration Significant differences between the untreated and the treated side according to the second evaluation method show the local effectiveness of a substance. According to the third evaluation, the point summation differences between the untreated control animals and the treated and untreated sides of the test animal group were evaluated, where again significant differences between control animals and the treated side of the test animals indicate the effect of a substance. Parallel thereto, a clear difference can also be seen as a rule between the untreated and the treated side of the test animal groups. But this difference is not always as clear as that between the control animals and the treated side, for which there may be many reasons, such as a mechanical transfer of a substance from one side to the other, or the influence of the solvent. In order to differentiate the effects according to evaluation methods 2 and 3, the following system was employed:

| Symbol | Point difference |
|---|---|
| ++ | very great (>99.9% probability) |
| + | significant (≧95% probability) |
| (+) | clear, but <95% probability |

The following Table 1 shows the evaluation results according to the above indicated system for the tested compounds B, C and G.

TABLE 1

| Evaluation of the sebosuppressive effects | | | |
|---|---|---|---|
| Substance according | Evaluation method | | |
| to preparation | 1 | 2 | 3 |
| B | ++ | ++ | ++ |
| C | + | (+) | (+) |
| G | ++ | ++ | + |
| 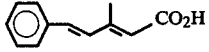 (US-PS 3 755 604) | 0 | 0 | + |

The following examples are for topical preparations according to the invention for the treatment of greasy hair and seborrheic skin.

EXAMPLE 1

| Skin cream | |
|---|---|
| Self-emulsifying mixture of mono/diglycerides of higher saturated fatty acids with potassium stearate, sold by Dehydag | 16.0 parts by weight |
| Cetyl/stearyl alcohol adducted with about 12 mols ethylene oxide | 1.0 parts by weight |
| 2-Octyldodecanol | 6.0 parts by weight |
| Isopropyl myristate | 4.0 parts by weight |
| Glycerin | 6.0 parts by weight |
| Compound according to Preparation A | 0.7 parts by weight |
| Water | 66.3 parts by weight |
| | 100.0 |

EXAMPLE 2

| Shampoo for greasy hair | |
|---|---|
| Ammonium lauryl sulfate, 33–35% Wash-active substance | 40.0 parts by weight |
| Coconut fatty acid diethanol amide | 3.0 parts by weight |
| Sodium chloride | 2.0 parts by weight |
| Sodium sulfate | 2.0 parts by weight |
| Compound according to Preparation B | 0.6 parts by weight |
| Perfume oil | 0.1 parts by weight |
| Water | 52.3 parts by weight |
| | 100.0 |

The preceding specific embodiments are illustrative of the practice of the invention. It is to be understood, however, that other expedients known to those skilled in the art or described herein, may be employed without departing from the spirit of the invention or the scope of the appended claims.

We claim:

1. A process for reducing sebaceous cell sebum production in a mammal in need thereof which comprises contacting said sebaceous cell in the skin of said mammal with an effective amount to reduce sebum production of at least one unsaturated aryl ketone compound having the formula

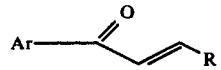

wherein Ar represents a member selected from the group consisting of phenyl, phenyl substituted with at least one group selected from the group consisting of alkyl having from 1 to 4 carbon atoms, alkoxy having from 1 to 4 carbon atoms, hydroxy and halo, and naphthyl, and R represents a member selected from the group consisting of hydrogen, alkyl having from 1 to 4 carbon atoms, alkanoyl having from 1 to 4 carbon atoms, aryl and arylcarbonyl, where aryl has the same meaning as Ar.

2. The process of claim 1 wherein said unsaturated aryl ketone compound is trans-1,2-dibenzoylethene.

3. The process of claim 1 wherein R is aryl, where aryl has the same meaning as Ar.

4. The process of claim 1 wherein R is arylcarbonyl, where aryl has the same meaning as Ar.

* * * * *